US011535137B2

United States Patent
Shimizu et al.

(10) Patent No.: US 11,535,137 B2
(45) Date of Patent: Dec. 27, 2022

(54) VEHICLE SEAT, VEHICLE SEAT CONTROL DEVICE, AND VEHICLE SEAT CONTROL METHOD

(71) Applicant: Panasonic Intellectual Property Management Co., Ltd., Osaka (JP)

(72) Inventors: Kazutaka Shimizu, Aichi (JP); Tsuyoshi Tanaka, Kyoto (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 268 days.

(21) Appl. No.: 17/031,177

(22) Filed: Sep. 24, 2020

(65) Prior Publication Data

US 2021/0101512 A1   Apr. 8, 2021

(30) Foreign Application Priority Data

Oct. 7, 2019 (JP) .............................. JP2019-184503
Jun. 3, 2020 (JP) .............................. JP2020-097095

(51) Int. Cl.
*B60N 2/90* (2018.01)
*B60N 2/00* (2006.01)
*B60Q 9/00* (2006.01)
*A61M 21/00* (2006.01)

(52) U.S. Cl.
CPC ............... *B60N 2/90* (2018.02); *A61M 21/00* (2013.01); *B60N 2/002* (2013.01); *B60Q 9/00* (2013.01); *A61M 2021/0022* (2013.01); *A61M 2021/0083* (2013.01); *A61M 2205/3344* (2013.01); *B60N 2002/981* (2018.02)

(58) Field of Classification Search
CPC .... B60N 2/90; B60N 2/002; B60N 2002/981; A61M 21/00; A61M 2021/0022; A61M 2021/0083; A61M 2205/3344; B60Q 9/00
USPC ............................................... 701/36
See application file for complete search history.

(56) References Cited

U.S. PATENT DOCUMENTS

| 10,399,492 | B1 * | 9/2019 | Paraskevas ............ B60N 2/002 |
| 10,562,412 | B1 * | 2/2020 | Main .................... A61B 5/0205 |
| 10,569,688 | B2 * | 2/2020 | Cansfield ................ B60N 3/02 |
| 11,046,225 | B2 * | 6/2021 | Mergl ................... A61H 23/02 |
| 2002/0014356 | A1 * | 2/2002 | Cech ................. B60R 21/01516 177/144 |
| 2013/0342335 | A1 * | 12/2013 | Mcqueen ................. G08B 6/00 340/436 |

(Continued)

FOREIGN PATENT DOCUMENTS

| JP | 2007-257505 | 10/2007 |
| JP | 2011-164825 | 8/2011 |
| JP | 2019-123263 | 7/2019 |

OTHER PUBLICATIONS

Office Action from Japan Patent Office (JPO) in Japanese Patent Appl. No. 2020-097095, dated Jul. 20, 2021, together with an English language translation.

*Primary Examiner* — Zhen Y Wu
(74) *Attorney, Agent, or Firm* — Greenblum & Bernstein, P.L.C.

(57) ABSTRACT

A vehicle seat includes: a pressure sensor capable of measuring a pressure distribution on a surface of the vehicle seat; a plurality of actuators provided in the vehicle seat; and a controller that controls vibrations generated by the plurality of actuators based on the pressure distribution output by the pressure sensor.

18 Claims, 13 Drawing Sheets

(56) References Cited

U.S. PATENT DOCUMENTS

| | | | |
|---|---|---|---|
| 2018/0057009 A1* | 3/2018 | Maeda | B62D 1/286 |
| 2018/0186251 A1* | 7/2018 | Yetukuri | B60N 2/976 |
| 2018/0297488 A1* | 10/2018 | Lem | B60N 2/002 |
| 2019/0193591 A1* | 6/2019 | Migneco | G06K 9/00536 |
| 2019/0337451 A1* | 11/2019 | Bacchus | B60Q 9/008 |
| 2020/0198465 A1* | 6/2020 | Tanabe | B60N 2/14 |
| 2021/0039537 A1* | 2/2021 | Kaku | A61B 5/1116 |
| 2021/0101547 A1* | 4/2021 | Nagata | A47C 1/024 |

\* cited by examiner

VEHICLE SEAT, VEHICLE SEAT CONTROL DEVICE, AND VEHICLE SEAT CONTROL METHOD

CROSS REFERENCE TO RELATED APPLICATIONS

The present application is based on and claims priority of Japanese Patent Application No. 2019-184503 filed on Oc. 7, 2019, and No. 2020-097095 filed on Jun. 3, 2020.

FIELD

The present disclosure relates to a vehicle seat, a vehicle seat control device, and a vehicle seat control method.

BACKGROUND

Conventionally, an alarm device that generates an alarm according to a driving state of a vehicle is known. Patent Literature (PLT 1) discloses a driving state alarm device including a vibration generating means (actuator) that generates vibrations as an alarm in a seat.

CITATION LIST

Patent Literature

PTL 1: Japanese Unexamined Patent Application Publication No. 2007-257505

SUMMARY

However, the operation status alarm device according to PTL 1 can be improved upon.

In view of this, the present disclosure provides a vehicle seat, a vehicle seat control device, and a vehicle seat control method capable of improving upon the above related art.

A vehicle seat according to an aspect of the present disclosure is a vehicle seat, comprising: a pressure sensor capable of measuring a pressure distribution on a surface of the vehicle seat; a plurality of actuators provided in the vehicle seat; and a controller that controls vibrations generated by the plurality of actuators based on the pressure distribution output by the pressure sensor.

A control device for a vehicle seat according to an aspect of the present disclosure is a control device for a vehicle seat, wherein the control device acquires a pressure distribution from a pressure sensor capable of measuring the pressure distribution on a surface of the vehicle seat, and controls vibrations generated by a plurality of actuators provided in the vehicle seat based on the pressure distribution acquired.

A method for controlling a vehicle seat according to an aspect of the present disclosure is a method for controlling a vehicle seat, comprising: acquiring a pressure distribution from a pressure sensor capable of measuring the pressure distribution on a surface of the vehicle seat; and controlling vibrations generated by a plurality of actuators provided in the vehicle seat based on the pressure distribution.

A vehicle seat and the like according to one aspect of the present disclosure is capable of improving upon the above related art.

BRIEF DESCRIPTION OF DRAWINGS

These and other advantages and features of the present disclosure will become apparent from the following description thereof taken in conjunction with the accompanying drawings that illustrate a specific embodiment of the present disclosure.

DESCRIPTION OF EMBODIMENTS

Figure 1A:
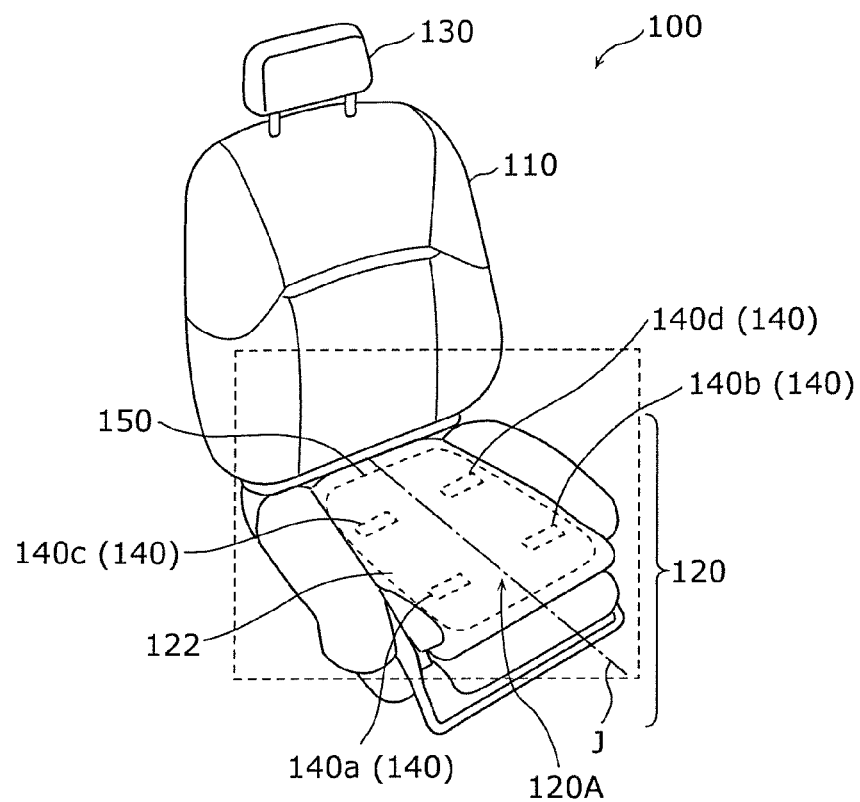
FIG. 1A is a diagram showing an appearance of a vehicle seat according to an embodiment.

Underlying Knowledge Forming Basis of the Present Disclosure

The inventors of the present application have found that the following problems occur with respect to the driving state alarm device of PTL 1 described in the "Background" section.

As described above, the driving state alarm device of PTL 1 is a device that has a vibration generating means (vibration generating device) provided into the seat and that gives a vibration alarm. The driving state alarm device, when generating a vibration as an alarm, can transmit the vibration as the alarm to the driver separately from other various vibrations generated during driving the vehicle by changing the frequency of the vibration with respect to the seat surface (pressure distribution) of the seat stepwise within a predetermined range.

By the way, the seat pressure on a vehicle seat varies depending on the position, posture, and physique of the person sitting on the vehicle seat. For that reason, if the vibration generating means uniformly applies a stimulus (vibration) to the person regardless of the position, posture, physique and the like of the person sitting on the vehicle seat, there is a difference in sitting state or individual difference in how the vibration is transmitted to the person, and there is a problem that it is difficult to obtain the intended effect (for example, transmitting a warning) due to the vibration. For example, in the technique of PTL 1, the vibration may not be properly transmitted to a sitting person.

In order to solve such a problem, a vehicle seat according to an aspect of the present disclosure is a vehicle seat including: a pressure sensor capable of measuring a pressure distribution on a surface of the vehicle seat; a plurality of actuators provided in the vehicle seat; and a controller that controls vibrations generated by the plurality of actuators based on the pressure distribution output by the pressure sensor.

With this, the vehicle seat may be able to generate vibrations in the actuators according to the pressure distribution. The pressure distribution changes depending on the position, posture, and physique of a person sitting on a vehicle seat. For that reason, the vehicle seat may be able to generate vibrations in the actuators according to the position, posture, and physique of the sitting person. Therefore, since there is a possibility that the vibrations can be appropriately transmitted to the sitting person according to the vehicle seat, there is a possibility that further improvement can be achieved. There is a possibility that the vehicle seat can appropriately transmit the vibrations to the sitting person, for example, as compared with the case where the vibrations generated by the actuators are not controlled according to the pressure distribution.

In addition, for example, when a variance value of the pressure distribution is smaller than a first threshold value, and a pressure value in the pressure distribution is equal to or larger than a second threshold value, the controller performs control to increase a strength of the vibration of each of the plurality of actuators.

With this, when a person sits down in a state (posture) in which the variance value of the pressure distribution is small, such as in a straight sitting posture, the vehicle seat can cause the actuators to generate vibrations according to the magnitude of the pressure value. That is, the vehicle seat can cause the actuators to generate vibrations according to the physique (for example, weight) of a person. Therefore, the vehicle seat can, in particular, transmit vibrations suitable for the physique (for example, weight) of the sitting person.

In addition, for example, when the variance value of the pressure distribution is larger than a predetermined value, the controller performs control to increase the strength of each of the vibrations of the actuators disposed in a portion where the pressure value of the pressure distribution is large.

With this, when a person is sitting in a state (posture) in which the variance value of the pressure distribution is large, such as a posture in which the person is leaning to one of the left and right, it is possible to generate a vibration corresponding to the portion with a large pressure value in the actuators. That is, the vehicle seat can cause the actuators to generate a vibration according to the posture of the person (for example, sitting leaning). Therefore, the vehicle seat can particularly transmit the vibration suitable for the posture of the sitting person.

In addition, for example, the controller controls the vibration of the plurality of actuators based on a warning signal from the outside.

With this, even when such a warning signal is transmitted to the person, the vehicle seat can appropriately transmit the warning signal to the person by controlling the actuators based on the pressure distribution.

In addition, for example, the controller controls at least one of the frequency or the strength of the vibration of the plurality of actuators based on the type of the warning signal.

With this, the vehicle seat can transmit the type of warning signal to a person depending on the vibration conditions of the actuators.

In addition, for example, when the pressure distribution does not substantially change over the first period, the controller controls the actuators with at least one of a frequency or a strength that reduces fatigue.

With this, the vehicle seat generates a vibration that reduces fatigue when the same posture continues for the first period. The vehicle seat can effectively transmit the vibration for reducing fatigue to a person by controlling the actuators based on the pressure distribution.

In addition, for example, when the pressure distribution fluctuates in a constant cycle within the second period, the controller controls the actuators by at least one of a frequency or a strength that promotes alertness.

With this, the vehicle seat can effectively transmit the vibration for promoting alertness to the person when the pressure distribution fluctuates in a constant cycle, that is, when the person is sleeping or has drowsiness.

In addition, for example, when the pressure width of the pressure distribution changes more than the third threshold within the third period, the controller controls the actuators at least one of a frequency or a strength that reduces fatigue.

With this, when a person sits down again, the vehicle seat generates a vibration that reduces fatigue because the person may be tired. The vehicle seat can effectively transmit the vibration for reducing fatigue to the person by controlling the actuators based on the pressure distribution.

In addition, for example, the controller invalidates the output of the pressure sensor while the actuators are generating vibration.

With this, the vehicle seat can exclude the change in the pressure distribution that the actuators give to the pressure sensor, and thus the possibility that the posture, physique and the like of a person may be erroneously determined due to the vibration can be reduced.

In addition, for example, the controller measures the pressure distribution based on an integrated pressure value during a predetermined measurement period at each coordinate point determined by the resolution of the pressure distribution of the pressure sensor.

With this, the vehicle seat integrates the amount of change in pressure for each coordinate point during the predetermined measurement period, so that the pressure distribution can be measured more accurately even with respect to the microscopic movement of the driver, and particularly the accuracy for the driver's fatigue judgment is improved.

In addition, for example, a control device for a vehicle seat acquires a pressure distribution from a pressure sensor capable of measuring the pressure distribution on a surface of the vehicle seat, and controls vibrations generated by a plurality of actuators provided in the vehicle seat based on the pressure distribution acquired.

This may be achieved the same effect as the vehicle seat described above.

In addition, for example, a method for controlling a vehicle seat includes: acquiring a pressure distribution from a pressure sensor capable of measuring the pressure distribution on a surface of the vehicle seat; and controlling vibrations generated by a plurality of actuators provided in the vehicle seat based on the pressure distribution.

This may be achieved the same effect as the vehicle seat described above.

It should be noted that these general or specific aspects may be realized by a system, a method, an integrated circuit, a computer program, or a non-transitory recording medium such as a computer-readable CD-ROM, and may be realized by any combination of a system, a method, an integrated circuit, a computer program, or a recording medium. The program may be stored in the recording medium in advance, or may be supplied to the recording medium via a wide area communication network including the Internet and the like.

Hereinafter, embodiments will be specifically described with reference to the drawings.

It should be noted that each of the embodiments described below shows a comprehensive or specific example. Numerical values, shapes, materials, components, arrangement positions and connection forms of components, steps, order of steps, and the like shown in the following embodiments are examples, and are not intended to limit the present disclosure. In addition, among the components in the following embodiments, components not described in independent claims are described as arbitrary components. In addition, each drawing is a schematic view, and is not necessarily strictly illustrated. In addition, in each drawing, the same reference numerals are given to the same component members.

In addition, in the present specification, a term indicating a relationship between elements such as equality and a numerical value are expressions that express not only a strict meaning but also expressions that mean to include a substantially equivalent range, for example, a difference of about several percent. In addition, the expressions using "substantially" such as "substantially unchanged" are used. For example, "substantially unchanged" means not only that it does not change at all, but also that it does not change substantially, that is, it includes a difference of, for example, about several percent (for example, a difference within an error range). In addition, the same applies to other expressions using "substantially".

Embodiment

Hereinafter, a vehicle seat according to the present embodiment will be described with reference to the drawings.

1. Configuration of Vehicle Seat

Figure 1B:
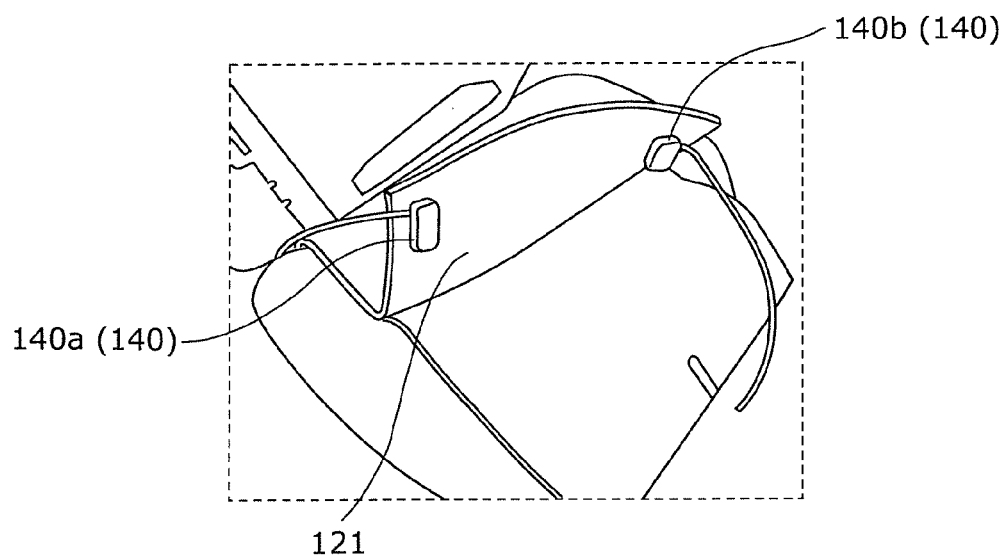
FIG. 1B is a diagram showing actuators included in the vehicle seat according to the embodiment.

First, the configuration of vehicle seat 100 according to the present embodiment will be described with reference to FIGS. 1A to 2. FIG. 1A is a diagram showing an outer appearance of vehicle seat 100 according to the present embodiment. FIG. 1B is a diagram showing actuators 140 included in vehicle seat 100 according to the present embodiment. FIG. 1B is a diagram showing a state where seat cover 122 is removed and a part of seat pad 121 is turned over in the broken line area of FIG. 1A.

As shown in FIGS. 1A and 1B, vehicle seat 100 includes seat back 110, seat cushion 120, headrest 130, a plurality of actuators 140, and pressure sensor 150.

Seat back 110 supports the back of a person who sits on vehicle seat 100. Headrest 130 supports the head of a person who sits on vehicle seat 100.

Seat cushion 120 supports the buttocks and thighs of a person who sits on vehicle seat 100. Such seat cushion 120 includes seat pad 121 corresponding to a cushion material and seat cover (skin cover) 122 that covers seat pad 121. Seat cover 122 is made of, for example, artificial leather and is disposed in a position corresponding to a person's buttocks and thighs. The upper surface of seat cushion 120 is seat surface 120A on which a person sits.

Actuators 140 are provided in vehicle seat 100 and have a configuration capable of applying vibrations to vehicle seat 100. In the present embodiment, vehicle seat 100 includes four actuators 140 (for example, actuators 140a to 140d). Actuators 140a and 140b are disposed inside seat cushion 120 so that the vibrations can be transmitted mainly to the thighs of a person. Actuator 140a is disposed, for example, on the front end side and the right side inside seat cushion 120, and actuator 140b is disposed, for example, on the front end side and the left side inside seat cushion 120.

In addition, actuators 140c and 140d are disposed inside seat cushion 120 so that the vibrations can be transmitted mainly to a person's buttocks. Actuator 140c is disposed, for example, on the rear end side and the right side inside seat cushion 120, and actuator 140d is disposed, for example, on the rear end side and the left side inside seat cushion 120.

In this way, the plurality of actuators 140 are provided, for example, in a one-to-one relationship with the left and right buttocks and the left and right thighs, respectively. In addition, the plurality of actuators 140 are disposed, for example, at positions symmetrical with respect to center line 3 that bisects seat surface 120A when seat cushion 120 is viewed from above (when viewed in plan). It should be noted that the arrangement position and the number of actuators 140 are not particularly limited as long as the arrangement position and the number can transmit the vibration to a person. In addition, at least one of the plurality of actuators 140 may be further disposed on at least one of seat back 110 or headrest 130.

As shown in FIG. 1B, actuators 140 are disposed, for example, on the lower surface side of seat pad 121. Actuators 140 are fixed, for example, to the lower surface of seat pad 121.

Actuators 140 are configured to include, for example, a motor. Actuators 140 are configured to include, for example, an eccentric motor that converts a rotational movement of the motor into a vibration. It should be noted that actuators 140 are not limited to include a motor as long as they can transmit desired vibrations to a person. For example, they may be actuators that use a piezoelectric effect, MEMS (Micro Electro Mechanical Systems) vibrators that use electrostatic force, or the like.

Pressure sensor 150 is a sensor that detects the seat pressure (pressure distribution) of a person on seat surface 120A. Pressure sensor 150 detects the pressure distribution of a person sitting on vehicle seat 100. Pressure sensor 150 is, for example, a pressure sensitive sensor. Pressure sensor 150 is, for example, provided so as to be able to measure the pressure distribution in a region including four actuators 140 in a plan view. Pressure sensor 150 may be capable, for example, of detecting the pressure distribution on seat surface 120A. Pressure sensor 150 may have, for example, a size that substantially coincides with seat surface 120A in a plan view. Pressure sensor 150 may be, for example, in the form of a flexible sheet.

Pressure sensor 150 may be provided, for example, on seat surface 120A or may be provided in seat cushion 120. In addition, pressure sensor 150 may be further provided on at least one of seat back 110 or headrest 130.

Here, the functional configuration of vehicle seat 100 will be described with further reference to FIG. 2. FIG. 2 is a block diagram showing a functional configuration of vehicle seat 100 according to the present embodiment. It should be noted that only one actuator 140 is illustrated in FIG. 2.

Figure 2:
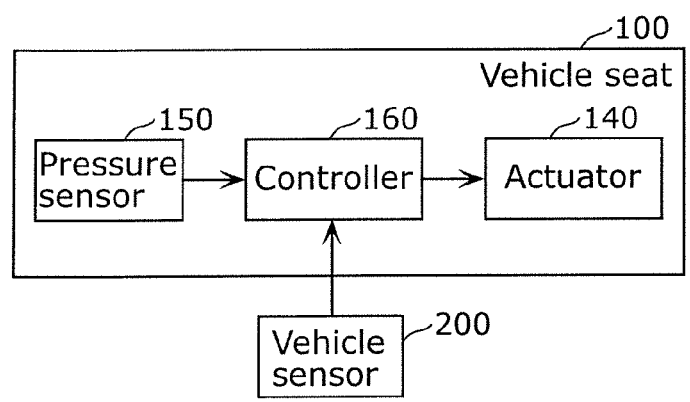
FIG. 2 is a block diagram showing a functional configuration of the vehicle seat according to the embodiment.

As shown in FIG. 2, vehicle seat 100 further includes controller 160.

Controller 160 is a control device that is electrically connected to each of the plurality of actuators 140 and pressure sensor 150, and controls vibrations generated by each of the plurality of actuators 140 based on the measurement result (for example, pressure distribution) output by pressure sensor 150. As the control of vibration, controller 160 determines the operating conditions of actuators 140 based on, for example, at least one of a pressure distribution or a pressure value in the pressure distribution. Determining the operating conditions includes determining actuators 140 to be vibrated among the plurality of actuators 140, determining the vibration conditions (vibration strength, frequency, etc.) of actuators 140, and the like. Controller 160 is an example of a control device that controls vehicle seat 100.

In addition, controller 160 acquires the detection result of vehicle sensor 200 from vehicle sensor 200 provided in the vehicle (for example, an automobile) in which vehicle seat 100 is mounted. Vehicle sensor 200 is a sensor that performs detection necessary for traveling of the vehicle, and may be, for example, a sensor for detecting whether or not the vehicle is traveling normally. Vehicle sensor 200 may be, for example, an imaging device such as a drive recorder, or a radar (for example, a millimeter wave radar) for detecting an object. In addition, vehicle sensor 200 may be a speed sensor that detects a speed, an acceleration sensor that detects an acceleration, a steering angle sensor that detects a steering angle, a position sensor that detects a position, an angular velocity sensor that detects a behavior of a vehicle, or the like. Furthermore, vehicle sensor 200 may be an imaging device that images an occupant. The imaging device may have a function of determining the state of the occupant (sleepiness, body fluctuation, etc.).

Figure 3A:
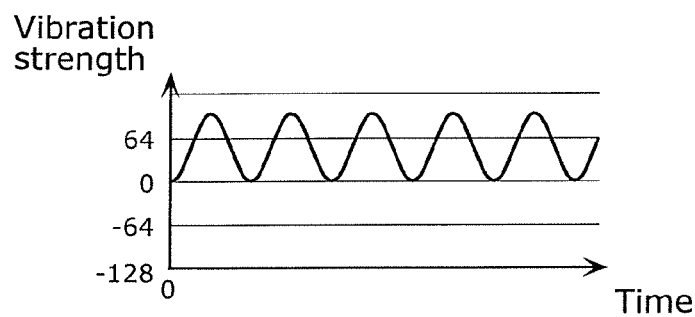
FIG. 3A is a diagram showing a first example of a vibration waveform generated by the actuator according to the embodiment.
Figure 3B:
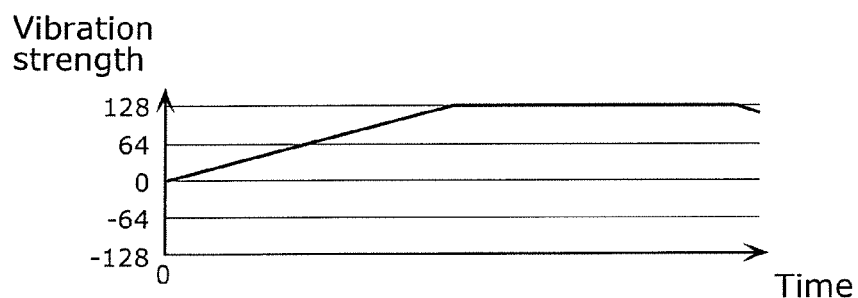
FIG. 3B is a diagram showing a second example of a vibration waveform generated by the actuator according to the embodiment.
Figure 3C:
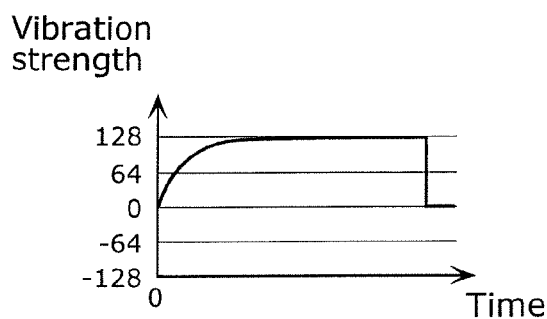
FIG. 3C is a diagram showing a third example of a vibration waveform generated by the actuator according to the embodiment.
Figure 3D:
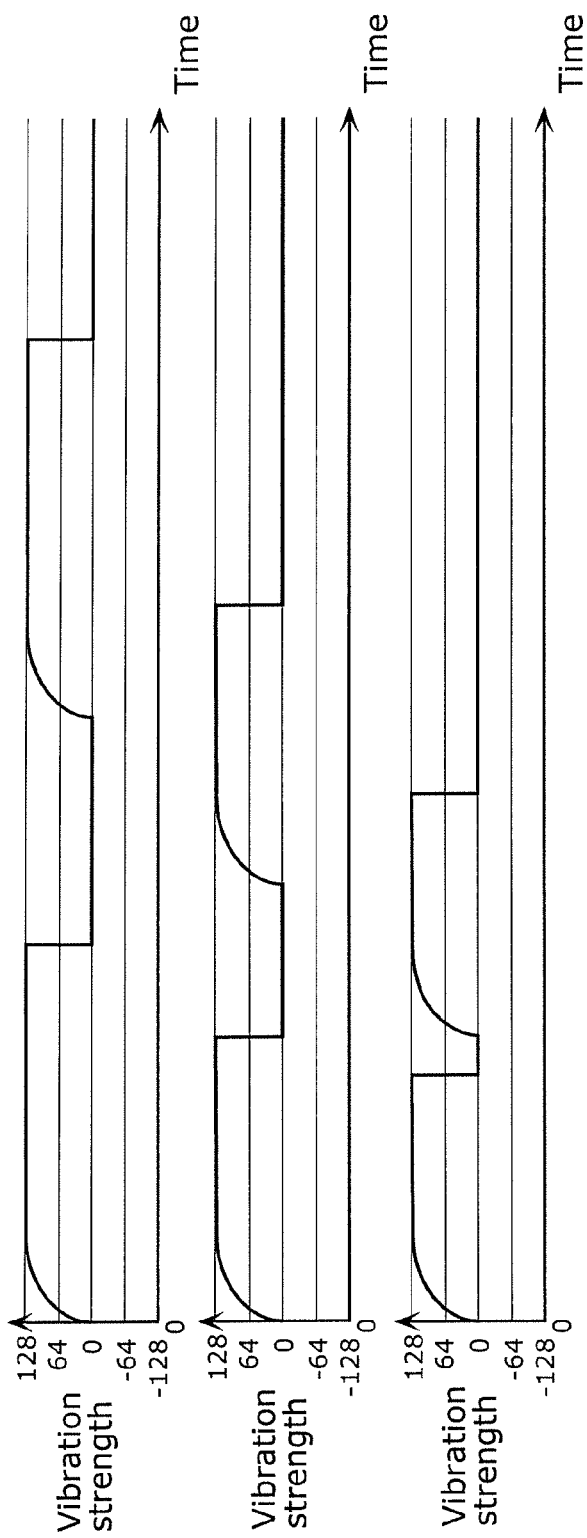
FIG. 3D is a diagram showing a fourth example of a vibration waveform generated by the actuator according to the embodiment.

Here, the vibration waveform of the vibrations generated by actuators 140 will be described with reference to FIGS. 3A to 3D. FIG. 3A is a diagram showing a first example of a vibration waveform generated by actuators 140 according to the present embodiment. FIG. 3B is a diagram showing a second example of a vibration waveform generated by actuators 140 according to the present embodiment. FIG. 3C is a diagram showing a third example of a vibration waveform generated by actuators 140 according to the present embodiment. FIG. 3D is a diagram showing a fourth example of a vibration waveform generated by actuators 140 according to the present embodiment. It should be noted that the vertical axis shown in FIGS. 3A to 3D represents vibration strength, and the horizontal axis represents time.

As shown in FIG. 3A, controller 160 may control actuators 140 to vibrate at a constant cycle. In other words, actuators 140 may vibrate at a constant cycle.

In addition, as shown in FIGS. 3B and 3C, controller 160 may control the vibration strength of actuators 140 so that it changes with time. In other words, actuators 140 may vibrate so that the vibration strength changes with time. Specifically, as shown in FIG. 3B, controller 160 may vibrate actuators 140 so as to include a period in which the vibration strength is linearly changed and a period in which the vibration strength is constant. In addition, as shown in FIG. 3C, controller 160 may vibrate actuators 140 so as to include a period in which the amount of change in the vibration strength is changed with time and a period in which the vibration strength is constant.

In addition, as shown in FIG. 3D, controller 160 may control actuators 140 so that the vibration condition of at least one actuator 140 of the plurality of actuators 140 differs from the vibration condition of the other actuators 140. For example, when the number of the plurality of actuators 140 are three, controller 160 may vibrate each of three actuators 140 under different vibration conditions as illustrated in FIG. 3D. It should be noted that although only the frequency is different among the vibration strength and the frequency in FIG. 3D, the vibration strength may be different from each other.

The vibration conditions shown in above FIGS. 3A to 3D are examples, and the present invention is not limited thereto.

2. Operation of Vehicle Seat

Next, the operation of vehicle seat 100 will be described with reference to FIGS. 4 to 10. In the following, such an example that controller 160 mainly controls the frequency as the vibration condition of actuators 140 is described, but at least one of the frequency or the vibration strength is only needed to be controlled.

Figure 4:
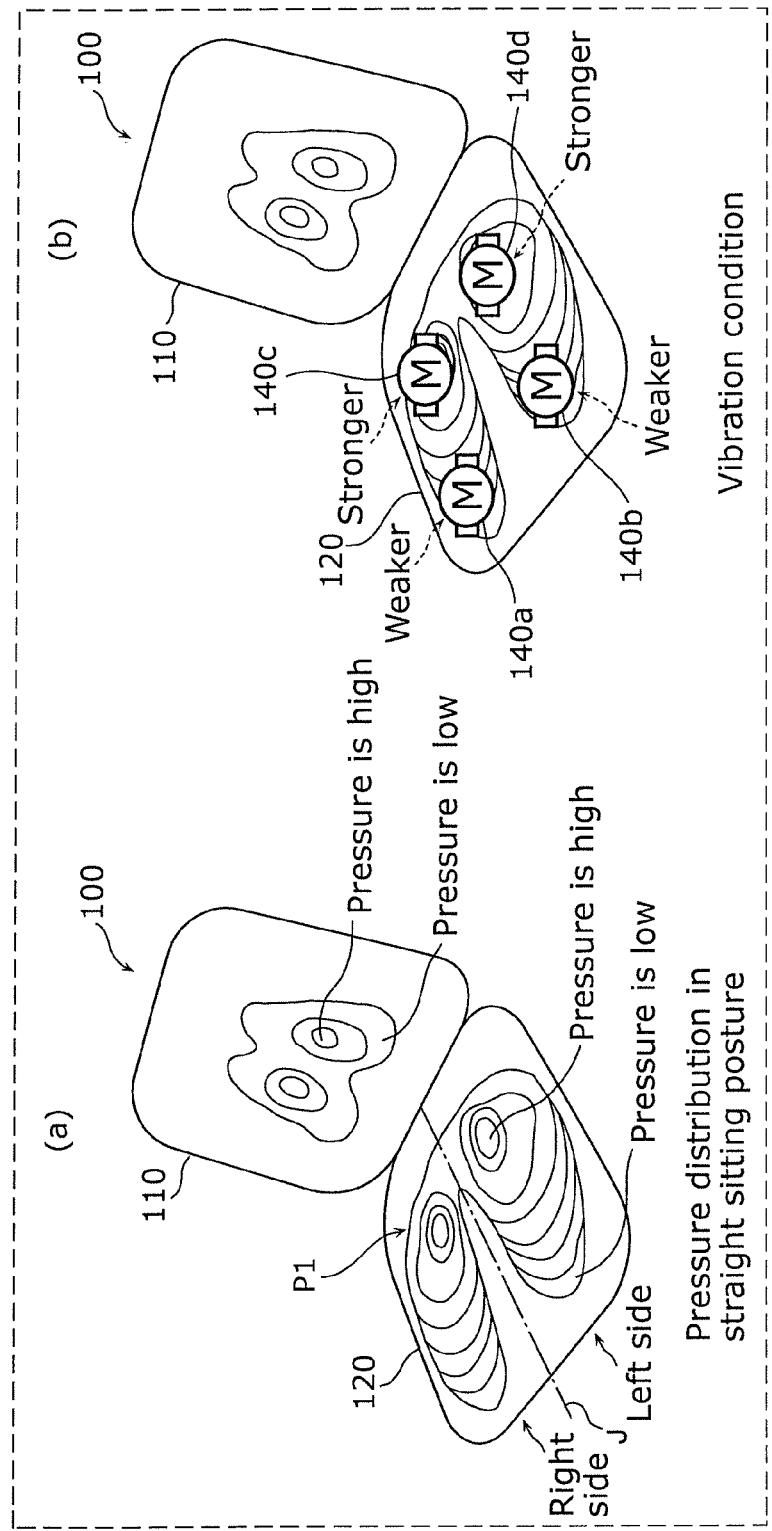
FIG. 4 is a diagram showing an example of a pressure distribution and vibration conditions of the vehicle seat according to the embodiment.

FIG. 4 is a diagram showing an example of pressure distribution P1 and vibration conditions of vehicle seat 100 according to the present embodiment. Specifically, FIG. 4 is a diagram for describing a case where a person is sitting on vehicle seat 100 in a straight sitting posture. (a) in FIG. 4 shows the measurement result of pressure sensor 150. (b) in FIG. 4 is a diagram in which actuators 140 are superimposed and displayed on (a) in FIG. 4 and shows the vibration condition of each of the plurality of actuators 140. In addition, when a person sits on vehicle seat 100, the right side with respect to center line J is also described as "right side" or "right", and the left side with respect to center line J is also described as "left side" or "left". It should be noted that the pressure distribution is schematically illustrated using contour lines in FIGS. 4 and 5.

As shown in (a) in FIG. 4, pressure distribution P1 has a symmetrical shape with respect to center line 3 in a plan view when a person is sitting on vehicle seat 100 in a straight sitting posture. In addition, in pressure distribution P1, the pressure values at the left and right buttocks are higher than those in other regions. In other words, according to pressure distribution P1, it is understood that the weight is applied to the positions of the left and right buttocks. For example, when pressure distribution P1 has a bilaterally symmetrical shape and the pressure values at the left and right buttocks are equal to or more than a predetermined value, it can be estimated that the person is in a straight sitting posture.

As shown in (b) in FIG. 4, controller 160 vibrates actuators 140c and 140d disposed in positions where the pressure value is high, that is, weight is applied to seat surface 120A, stronger than the other actuators 140a and 140b. For example, controller 160 may vibrate actuators 140c and 140d stronger than the reference vibration strength, and may vibrate actuators 140a and 140b weaker than the reference vibration strength.

In this way, controller 160 can effectively transmit the vibrations to a person by vibrating strongly actuators 140 around the position where the pressure is applied.

Figure 5:
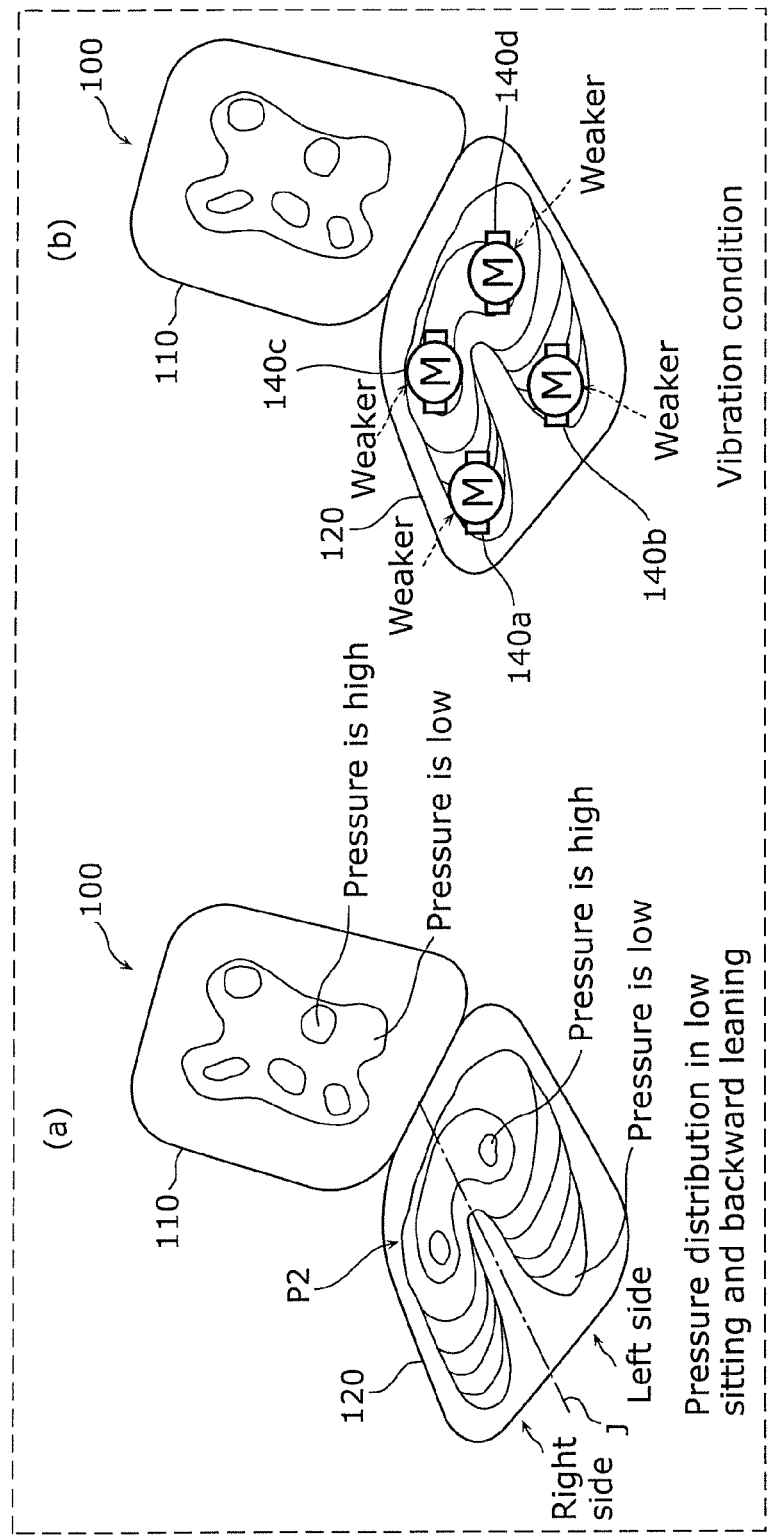
FIG. 5 is a diagram showing another example of the pressure distribution and the vibration conditions of the vehicle seat according to the embodiment.

FIG. 5 is a diagram showing another example of pressure distribution P2 and vibration conditions of vehicle seat 100 according to the present embodiment. Specifically, FIG. 5 is a diagram for describing a case in which a person is sitting on vehicle seat 100 in a low sitting and backward leaning posture. (a) in FIG. 5 shows the measurement result of pressure sensor 150, and (b) in FIG. 5 is a diagram in which actuators 140 are superimposed and displayed on (a) in FIG. 5 to show the vibration conditions of each of actuators 140.

As shown in (a) in FIG. 5, pressure distribution P2 has a symmetrical shape with respect to center line 3 in a plan view when a person is sitting on vehicle seat 100 in a low sitting and backward leaning posture. However, the pressure value indicated by pressure distribution P2 is lower mainly at the buttocks as compared with (a) in FIG. 4. In other words, the weight is not mainly applied to the positions of the left and right buttocks in pressure distribution P2. For example, when pressure distribution P2 has a bilaterally symmetric shape and the pressure value is generally low, it can be inferred that the person is in a low sitting and backward leaning posture. It should be noted that the low sitting and backward leaning posture is, for example, a posture in which a person sits shallowly on vehicle seat 100 and is leaning on seat back 110.

As shown in (b) in FIG. 5, controller 160 vibrates all of actuators 140*a* to 140*d* weakly because the pressure value is low, that is, no weight is applied to seat surface 120A. For example, controller 160 may vibrate all actuators 140*a* to 140*d* weaker than the reference vibration strength.

In this way, controller 160 weakly vibrates actuators 140 around the position where the applied pressure is low, so that the vibration can be effectively transmitted to a person while suppressing the power consumption.

Figure 6:
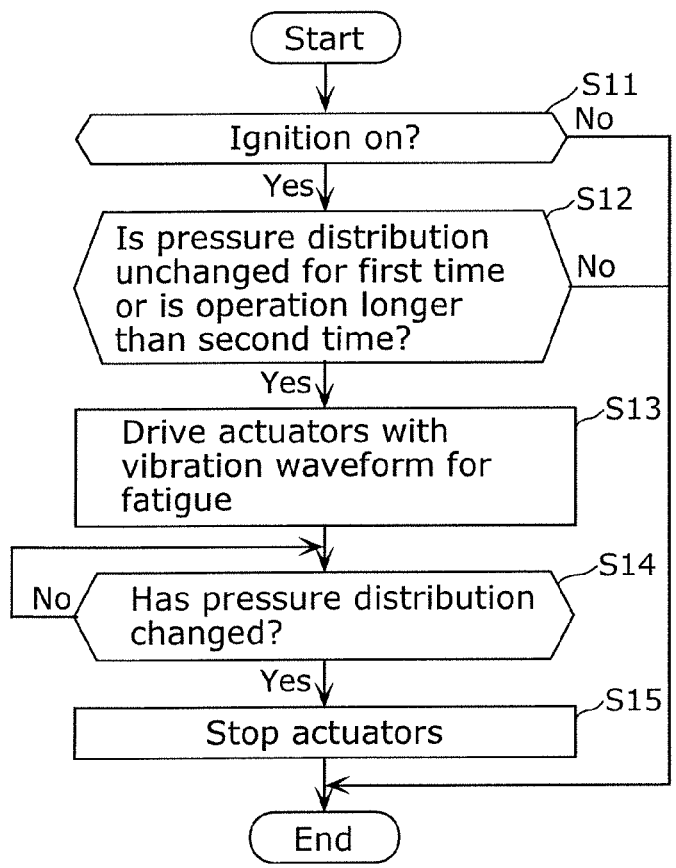
FIG. 6 is a flowchart showing a first example of the operation of the vehicle seat according to the embodiment.

Subsequently, the operation of vehicle seat 100 when detecting fatigue will be described with reference to FIG. 6. FIG. 6 is a flowchart showing a first example of the operation of vehicle seat 100 according to the present embodiment. It should be noted that an example in which a person sitting on vehicle seat 100 is a driver will be described in the following, but the present invention is not limited thereto. The person sitting on vehicle seat 100 may be, for example, a person on board, a passenger or the like.

As shown in FIG. 6, controller 160 determines whether or not the ignition is turned on (IG/ON) in the vehicle (S11). Controller 160 may determine whether or not the ignition is turned on in the vehicle, for example, based on the signal acquired from vehicle sensor 200.

When the ignition is turned on in the vehicle (Yes in S11), controller 160 starts pressure measurement by pressure sensor 150, and proceeds to step S12. In addition, controller 160 finishes the process, when the ignition is not turned on in the vehicle (No in S11).

Pressure sensor 150 measures the pressure after the ignition is turned on in the vehicle. For example, pressure sensor 150 may measure the pressure at predetermined time intervals, or may measure the pressure sequentially. Pressure sensor 150 outputs a pressure distribution indicating the measured pressure to controller 160.

Controller 160 determines whether or not the pressure distribution acquired from pressure sensor 150 is in a state where there is no change for the first time, or whether or not the driving exceeds the second time (S12).

First, a description will be given of how controller 160 determines whether or not there is no change in the pressure distribution for the first time. Controller 160 determines that the driver is tired when there is no change in the pressure distribution for the first time (Yes in S12), that is, when the driver has substantially the same posture for the first time. This is because if the posture is substantially the same for the first time, the driver may be tired because the muscles are hardened. In addition, when there is a change in the pressure distribution within the first time (No in S12), controller 160 ends the process.

It should be noted that the fact that there is a change in the pressure distribution may be, for example, a change in the position of the peak value of the pressure in the pressure distribution measured by pressure sensor 150. In addition, for example, the fact that there is a change in the pressure distribution may mean that the distribution in the region of a predetermined pressure value or more in the pressure distribution changes. The change in the pressure distribution may be, for example, a change from a state in which the regions are located on both the left and right sides to a state in which the regions are located on one side of the left and right sides, that is, a change from the straight sitting posture to the one-sided leaning posture.

In addition, the fact that there is a change in the pressure distribution may be, for example, a change in the area ratio of the regions having a predetermined pressure value or more in the left and right pressure distributions by 1:2 or more. The fact that there is a change in the pressure distribution may be, for example, a change from a state in which the area of the region on the left side is equal to or less than half the area of the region on the right side to a state in which the area of the region on the left side is twice or more the area of the region on the right side, that is, it may change from a posture leaning to the left to a posture leaning to the right.

In addition, the fact that there is no change in the pressure distribution in the above includes that it does not substantially change. In the following, it is also described that there is substantially no change.

The first time is a period of time shorter than the second time. The first time may be, for example, a time at which the driver starts feeling tired or may be a time shorter than a time at which the driver starts feeling tired. The first time may be, for example, 20 minutes, 15 minutes, or 10 minutes. The first time is the elapsed time after the pressure distribution has not changed. It should be noted that the first time is an example of the first period.

Next, a description will be given of how controller 160 determines whether or not the driving exceeds the second time. When the driving exceeds the second time (Yes in S12), controller 160 determines that the driver is tired because the driver has been driving for a long time. In addition, when the driving does not exceed the second time (No in S12), controller 160 ends the process.

The second time is a time longer than the first time. The second time may be, for example, a time at which the driver starts to feel fatigue due to continuous driving, or may be a time shorter than a time at which the driver starts to feel fatigue. The second time may be, for example, 45 minutes, 60 minutes, or 75 minutes. In addition, the second time may be, for example, an elapsed time after the ignition is turned on, or an elapsed time after the stopped state continues for a predetermined time or more. The predetermined time is a time when the driver is expected to take a break.

In addition, the second time may be an accumulated value of the time when it is determined that there is a change in the pressure distribution within the first time (No in S12). When the first time is minutes and the second time is 60 minutes, if such a determination that there is no change in the pressure distribution for the first time occurs four times consecutively, controller 160 may determine that the driving exceeds the second time (Yes in S12).

It should be noted that in step S12, controller 160 may determine whether or not there is no change at least in the pressure distribution for the first time.

Next, when it is determined as Yes in step S12, controller 160 drives actuators 140 with a vibration waveform for fatigue (S13). The vibration waveform for fatigue may be a vibration waveform that can recover the fatigue of the driver, and for example, may be a vibration having a frequency sufficient for improving the blood flow of the driver. The vibration waveform for fatigue has a higher frequency than the vibration waveform for alertness described later, and for example, the frequency may be 70 Hz or higher, more preferably 80 Hz or higher, and further preferably 90 Hz or higher. In addition, the vibration waveform for fatigue may be a vibration having such a vibration strength as to be able to recover the fatigue of the driver. It should be noted that step S13 is an example of the control step.

For example, controller 160 may vibrate actuators 140 under the vibration conditions of the vibration waveform vibrating as shown in FIG. 3A and the frequency of 70 Hz, or may vibrate actuators 140 under the vibration conditions of the vibration waveform vibrating as shown in FIG. 3B and the frequency of 70 Hz.

It should be noted that when the second time is an accumulated value of the time in which it is determined that there is a change in the pressure distribution within the first time (No in S12), even when there is a change in the pressure distribution, after the second time has elapsed, actuators 140 are automatically operated with the vibration waveform for fatigue. Controller 160 can recover the fatigue of the driver before the fatigue accumulates in the driver, for example, by setting the second time to a time shorter than the time when the driver starts to get tired.

Next, controller 160 determines whether or not there is a change in the pressure distribution acquired from pressure sensor 150 after actuators 140 have been driven with the vibration waveform for fatigue (S14). Whether or not there is a change in the pressure distribution here may be determined, for example, by the same criterion as the determination as to whether or not there is a change in the pressure distribution in step S12. When there is a change in the pressure distribution (Yes in S14), that is, when the driver moves due to the vibration of actuators 140, controller 160 stops actuators 140 (S15) and ends the process. This is because it is possible to determine that the fatigue of the driver has recovered due to the movement of the driver. It should be noted that controller 160 stops, for example, all of the plurality of actuators 140 in step S15.

In addition, when there is no change in the pressure distribution (No in S14), controller 160 continues to drive actuators 140 with the drive waveform for fatigue. It should be noted that, for example, when it is determined as No in step S14, controller 160 may further increase the vibration strength of the vibration of actuators 140 or may increase the frequency.

Figure 7:
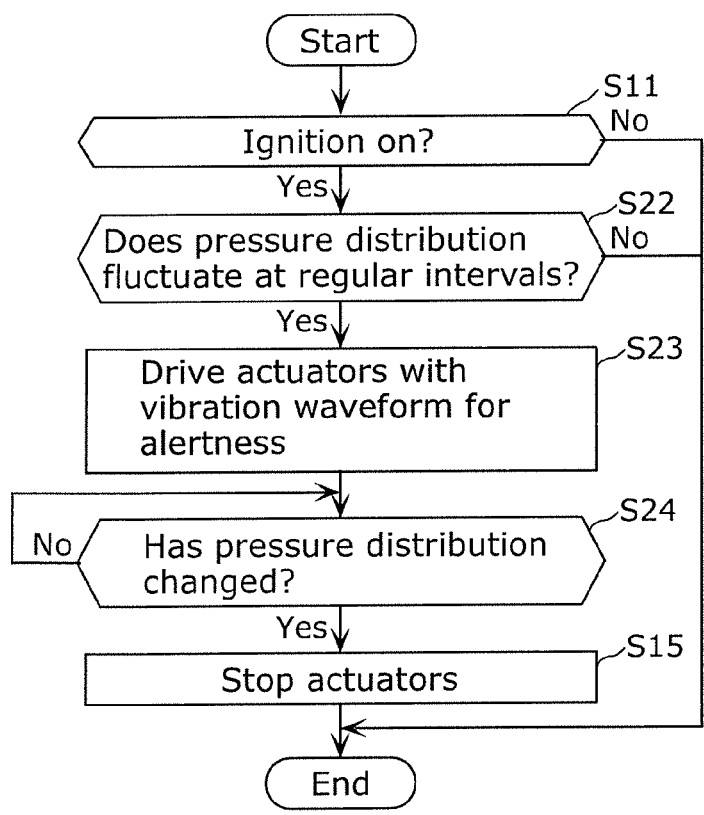
FIG. 7 is a flowchart showing a second example of the operation of the vehicle seat according to the embodiment.

Subsequently, the operation of vehicle seat 100 when detecting alertness will be described with reference to FIG. 7. FIG. 7 is a flowchart showing a second example of the operation of vehicle seat 100 according to the present embodiment.

As shown in FIG. 7, when the ignition is turned on in the vehicle (Yes in S11), controller 160 determines whether or not the pressure distribution fluctuates in a constant cycle within the second period (S22). The fact that the pressure distribution fluctuates in a constant cycle is that, for example, changes in the pressure distribution on the left and right occur at substantially the same time intervals. The fact that the pressure distribution fluctuates in a constant cycle may be, for example, a state in which peak values of pressure are alternately generated in the left and right regions at substantially the same time intervals. In addition, the fact that the pressure distribution fluctuates in a constant cycle may be, for example, a state in which regions having pressure values equal to or higher than a predetermined value are alternately generated in the left and right regions at substantially the same time intervals. In addition, the fact that the pressure distribution fluctuates in a constant cycle may be, for example, changes in the pressure distribution in the front-rear direction occur at substantially the same time intervals. It should be noted that the second period may be, for example, 30 minutes, 20 minutes, or 10 minutes.

When the pressure distribution fluctuates in a constant cycle (Yes in S22), controller 160 drives actuators 140 with the vibration waveform for alertness (S23). The vibration waveform for alertness may be a vibration waveform that can reduce drowsiness of the driver, that is, a vibration waveform that can promote alertness to the driver. Furthermore, the vibration waveform for alertness may be a vibration waveform having a frequency and a vibration strength in a range that does not cause a discomfort to the sitting driver. The vibration waveform for alertness has a lower frequency than the vibration waveform for fatigue, and the frequency is, for example, 50 Hz or less, more preferably 30 Hz or less, and further preferably 15 Hz or more and 30 Hz or less. In addition, the vibration waveform for alertness may be a vibration having a strength that can promote alertness to the driver. It should be noted that step S23 is an example of the control step.

Controller 160 may vibrate actuators 140 under the vibration conditions of the vibration waveform vibrating as shown in FIG. 3C and the frequency of 30 Hz, or may vibrate them under the vibration conditions of the vibration waveform as shown in FIG. 3D and the frequency of 30 Hz.

Next, controller 160 determines whether or not there is a change in the pressure distribution acquired from pressure sensor 150 after actuators 140 has been driven with the vibration waveform for alertness (S24). The fact that there is a change in the pressure distribution here means, for example, that the fluctuation of the pressure distribution when it is determined as Yes in step S22 does not continue. The fact that there is a change in the pressure distribution may be, for example, that there is a change from the fluctuation of the pressure distribution when it is determined as Yes in step S22. The fact that there is a change in the pressure distribution may be that the fluctuation of the pressure distribution having a constant cycle has changed to the fluctuation of the pressure distribution having no constant cycle. In addition, the fact that there is a change in the pressure distribution may be that the fluctuation in the pressure distribution has stopped.

When there is a change in the pressure distribution (Yes in S24), that is, when the driver moves due to the vibration of actuators 140, controller 160 stops actuators 140 (S15) and ends the process.

This is because it can be determined that the driver has got alertness due to the movement of the driver.

In addition, when there is no change in the pressure distribution (No in S24), controller 160 continuously drives actuators 140 with the drive waveform for alertness. It should be noted that for example, when it is determined as No in step S24, controller 160 may further increase the vibration strength of actuators 140 or may increase the frequency.

It should be noted that the fluctuation of the driver is determined based on the fluctuation of the pressure distribution in the operation of FIG. 7, but in addition thereto, the fluctuation of the driver may be also determined by the imaging device (vehicle sensor 200) that images the driver. In this case, the fluctuation of the driver can be detected in the whole body, so that the determination can be made more accurately.

Figure 8:
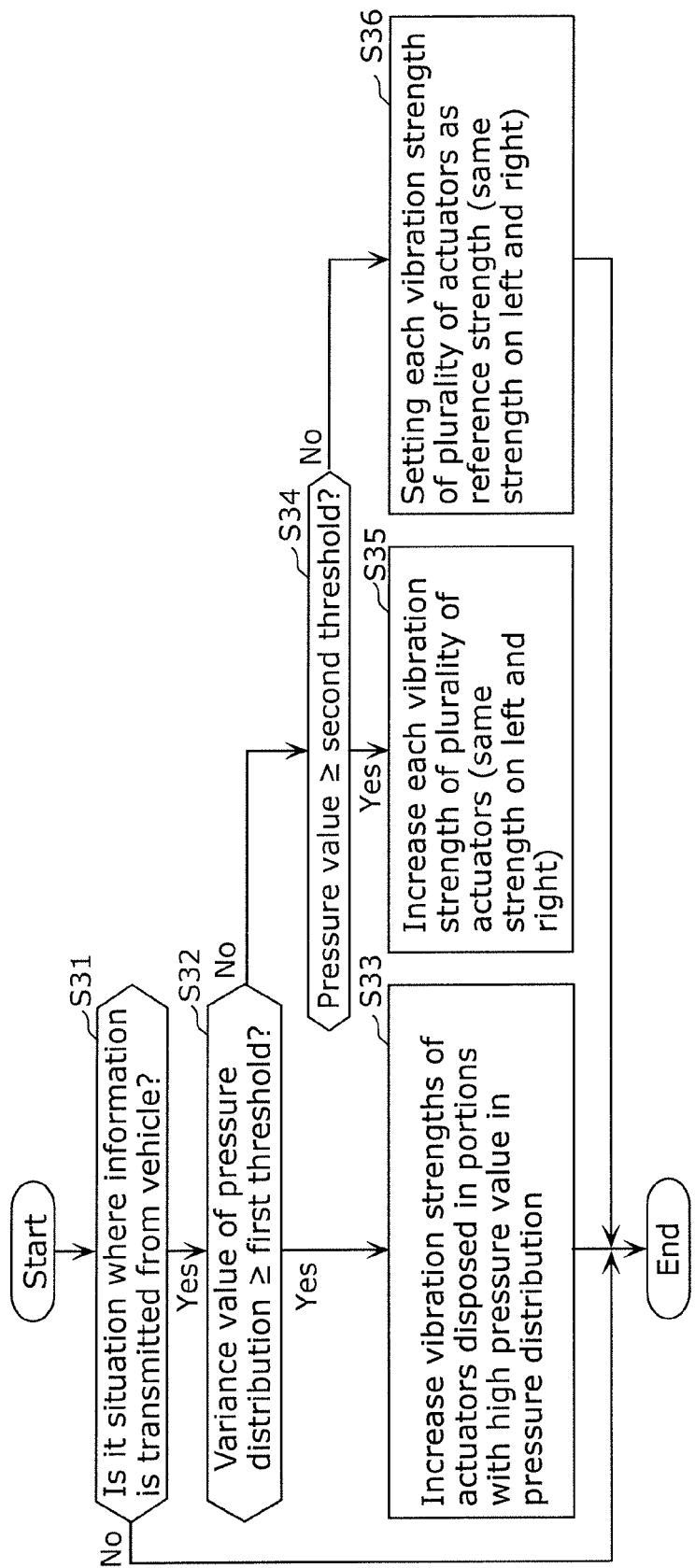
FIG. 8 is a flowchart showing a third example of the operation of the vehicle seat according to the embodiment.

Subsequently, an example of an operation at the time of transmitting information in vehicle seat 100 will be described with reference to FIG. 8. FIG. 8 is a flowchart showing a third example of the operation of vehicle seat 100 according to the present embodiment. FIG. 8 shows an operation when transmitting information about the vehicle acquired from vehicle sensor 200 or the like and which needs to be notified to the driver using vibration.

As shown in FIG. 8, controller 160 determines whether or not it is under the situation that information is transmitted from the vehicle (S31). For example, when controller 160 acquires information indicating a driving danger from vehicle sensor 200, controller 160 determines that it is under the situation that the vehicle transmits the information to the driver. The information indicating danger may be, for example, information indicating that the vehicle is travelling at an excessive speed, that a following vehicle is approaching, information indicating that the vehicle is on the center line, or information indicating that an obstacle (for example, a pedestrian, a wall, etc.) is present in the front or the rear. Such information is an example of a warning signal from the outside of vehicle seat 100.

When the vehicle is in a state of transmitting information to the driver (Yes in S31), controller 160 determines whether the dispersion value of the pressure distribution acquired from pressure sensor 150 is equal to or more than the first threshold value (S32). The first threshold value is not particularly limited as long as it is a value that can determine whether or not a person is in a straight sitting posture. It can also be said that controller 160 determines in step S32 whether or not the sitting person is in the straight sitting posture depending on whether or not the pressure distribution is biased. The state in which the pressure distribution is biased is, for example, a state in which the left and right pressure distributions are different. The state in which the pressure distribution is biased may be, for example, a state in which the pressure distribution is not bilaterally symmetric, a state in which the area ratios of regions having pressure values equal to or higher than a predetermined value differ by 1.2 times or more on the left and right, or a state in which the position of the peak value of the pressure may be different between the left and the right.

It should be noted that the example of comparing the variance value of the pressure distribution and the first threshold value in step S32 has been described, but the present invention is not limited thereto. Controller 160 may compare the value indicating the distribution degree of the pressure distribution with the first threshold value. The value indicating the degree of distribution may be, for example, the median value, the average value, the standard deviation or the like of pressure, or the difference between the maximum value and the minimum value. It should be noted that hereinafter, the difference between the maximum value and the minimum value of the pressure in the pressure distribution is also described as the width of the pressure distribution.

Next, when the variance value of the pressure distribution is equal to or higher than the first threshold value (Yes in S32), controller 160 increases the vibration strength of actuators 140 disposed in a portion where the pressure value of the pressure distribution is high among the plurality of actuators 140 (S33). The portion where the pressure value of the pressure distribution is high (a portion having a large pressure value) means, for example, a region having a predetermined pressure value or more. The predetermined pressure value may be, for example, a value capable of determining whether or not the weight of the driver is equal to or more than a predetermined value. It can also be said that controller 160 controls the vibration strength of actuators 140 according to the pressure distribution when the person is not in a straight sitting posture (for example, when the person is sitting leaning).

Controller 160 may, for example, make the vibration strength of actuators 140 disposed in a portion having a high pressure value higher than the vibration strength of actuators 140 disposed in another portion. In addition, controller 160, for example, may make the vibration strength of actuators 140 disposed in a portion having a high pressure value higher than the reference vibration strength. In addition, controller 160, for example, may make the vibration strength of actuators 140 disposed in a portion having a high pressure value higher than the reference vibration strength and the vibration strength of actuators 140 disposed in a portion having a low pressure value lower than the reference vibration strength.

With this, actuators 140 on the side where the pressure is strongly applied can be vibrated strongly, so that the certainty that the vibration according to the information from the vehicle can be transmitted to the driver is increased.

It should be noted that controller 160 may change the vibration strength of actuators 140 in step S33 according to the left and right difference in the pressure distribution. For example, controller 160 may increase the vibration strength of actuators 140 on the higher side of the pressure distribution as the left and right difference in the pressure distribution increases. It should be noted that the left and right difference in the pressure distribution may be an area difference in the area of the region with the pressure value of a predetermined value or more on each of the left and right, a difference in the position of the peak value of the pressure, or a difference in the peak value.

In addition, when the variance value of the pressure distribution is not equal to or higher than the first threshold value (No in S32), controller 160 determines whether or not the pressure value of the pressure distribution is equal to or higher than the second threshold value (S34). The second threshold value is not particularly limited as long as it is a value capable of determining whether or not the weight of the sitting person is equal to or greater than a predetermined value. It can also be said that controller 160 determines whether the weight of the sitting person is heavy or light in step S34. It should be noted that the pressure value of the pressure distribution is a representative pressure value of the pressure distribution, and may be any of the maximum value, the median value, the average value, and the minimum value of the pressure.

Assuming that the postures of the heavy weight person and the light weight person are the same, when the heavy weight person sits on vehicle seat 100, the pressure value of the pressure distribution is generally higher than that when the light weight person sits on vehicle seat 100. The pressure distribution when a heavy person sits on vehicle seat 100 has, for example, a distribution similar to that of (a) in FIG. 4.

When the pressure value of the pressure distribution is equal to or higher than the second threshold value (Yes in S34), controller 160 performs control to increase the vibration strength of each of the plurality of actuators 140 (S35). For example, controller 160 performs control to increase the strength of vibration of each of the plurality of actuators 140 as compared with the case where it is determined as Yes in step S32. Controller 160 controls, for example, step S35 so that actuators 140 (for example, actuators 140a and 140b) disposed on the left and right have the same strength. Controller 160, for example, performs control to increase the vibration strength of each of the plurality of actuators 140 while maintaining the state in which actuators 140*a* and 140*b* have the same strength and actuators 140*c* and 140*d* have the same strength.

It should be noted that in step S35, controller 160 may perform control such that the higher the pressure value of the pressure distribution, the stronger the vibration strength of each of actuators 140.

In addition, the pressure distribution when a person with a light weight sits on vehicle seat 100 has, for example, a distribution similar to that of (a) in FIG. 5.

When the pressure value of the pressure distribution is lower than the second threshold value (No in S34), controller 160 controls the vibration strength of each of the plurality of actuators 140 as the reference strength (S36). For example, controller 160 performs control to weaken the strength of vibration of each of the plurality of actuators 140 as compared with the case where it is determined as Yes in step S34. Controller 160 controls step S36 so that actuators 140 disposed on the left and right have the same strength. Controller 160, for example, performs control to set the vibration strength of each of the plurality of actuators 140 to be a reference strength while maintaining the state in which actuators 140*a* and 140*b* have the same strength and actuators 140*c* and 140*d* have the same strength.

It should be noted that in step S36, controller 160 may perform control such that the lower the pressure value of the pressure distribution, the weaker the vibration strength of each of actuators 140.

In this way, when the pressure distribution is not biased, controller 160 may control the strength of vibration of actuators 140 according to the weight. With this, the vibration can be reliably transmitted to the driver with a heavy weight, and the information from the vehicle can be transmitted to the driver with a light weight while suppressing the power consumption of actuators 140.

Note that steps S33 to S36 are examples of control steps.

Figure 9:
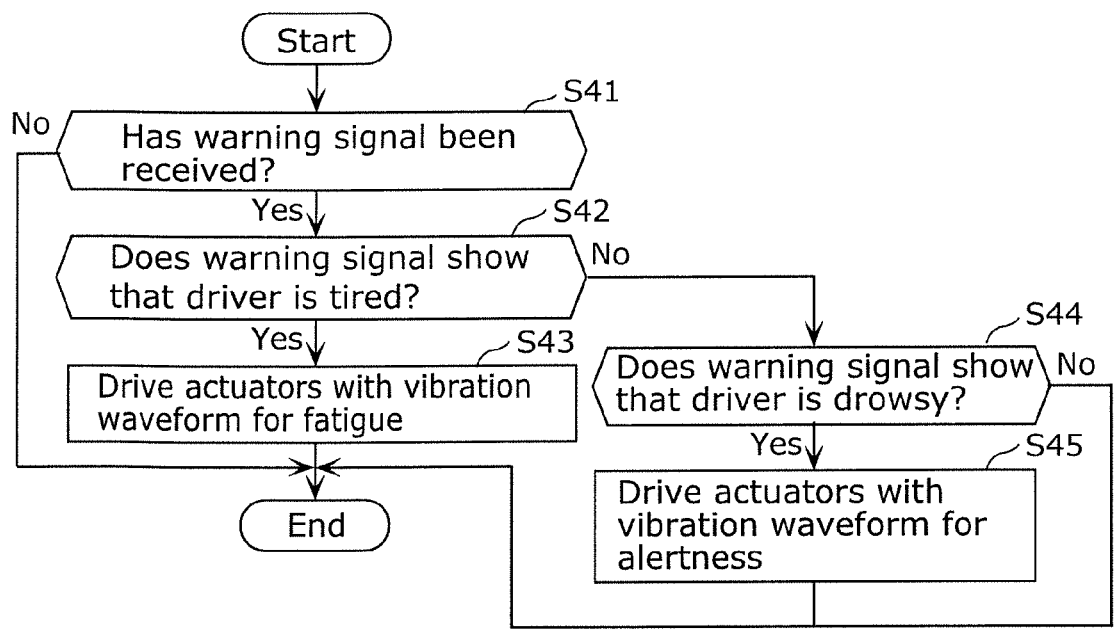
FIG. 9 is a flowchart showing a fourth example of the operation of the vehicle seat according to the embodiment.

Subsequently, another example of the operation at the time of transmitting information in vehicle seat 100 will be described with reference to FIG. 9. FIG. 9 is a flowchart showing a fourth example of the operation of vehicle seat 100 according to the present embodiment. FIG. 9 shows an operation when controller 160 acquires, as a warning signal, information indicating a driver state such as the driver being tired or having drowsiness. It should be noted that such a warning signal is generated, for example, based on an image captured by an image capturing device (vehicle sensor 200) that captures an image of the inside of a vehicle.

As shown in FIG. 9, controller 160 determines whether or not a warning signal has been acquired from the vehicle (S41). When the warning signal is acquired from vehicle sensor 200 (Yes in S41), controller 160 determines whether or not the warning signal includes information indicating that the driver is tired (S42). Then, when the warning signal includes information indicating that the driver is tired (Yes in S42), controller 160 drives actuators 140 with the vibration waveform for fatigue (S43). The vibration waveform in step S43 is, for example, the vibration waveform described in step S13 of FIG. 13.

In addition, when the warning signal does not include information indicating that the driver is tired (No in S42), controller 160 determines whether or not the warning signal includes information indicating that the driver has drowsiness (S44). Then, when the warning signal includes information indicating that the driver has drowsiness (Yes in S44), controller 160 drives actuators 140 with the vibration waveform for alertness (S45). The vibration waveform in step S45 is, for example, the vibration waveform described in step S23 of FIG. 7.

In this way, controller 160 may control the vibration conditions of the plurality of actuators 140 based on the type of a warning signal.

Figure 10:
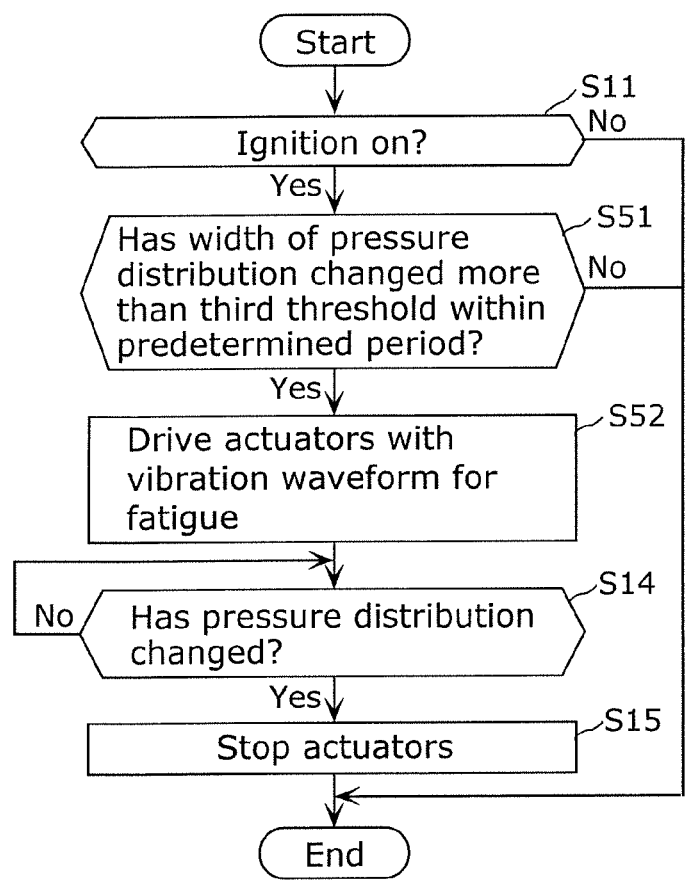
FIG. 10 is a flowchart showing a fifth example of the operation of the vehicle seat according to the embodiment.

Subsequently, the operation when the driver sits down again on vehicle seat 100 will be described with reference to FIG. 10. FIG. 10 is a flowchart showing a fifth example of the operation of vehicle seat 100 according to the present embodiment.

As shown in FIG. 10, when the ignition is turned on in the vehicle (Yes in S11), controller 160 determines whether or not the width of the pressure distribution has changed more than the third threshold value within a predetermined time (S51). The width of the pressure distribution is, for example, the difference between the maximum value and the minimum value of the pressure indicated by the pressure distribution. In addition, the third threshold value is not particularly limited as long as it can be determined that the driver sits down again. It can also be said that controller 160 determines, for example, whether or not the driver sits down again in step S51. Controller 160 determines, for example, whether or not actuators 140 do not vibrate and the driver spontaneously sits down again. It should be noted that the predetermined time here is an example of the third period. In addition, the width of the pressure distribution is an example of the pressure width.

Controller 160 may make the determination in step S51 by using, for example, the width of the pressure distribution in the right region and the width of the pressure distribution in the left region. For example, when the width of the pressure distribution on the right side changes more than the third threshold value and the width of the pressure distribution on the left side changes more than the third threshold value within a predetermined time, controller 160 may determine that the width of the distribution has changed more than the third threshold within the predetermined time.

When it is determined that the width of the pressure distribution has changed more than the third threshold value within the predetermined time (Yes in S51), controller 160 drive actuators 140 with the vibration waveform for fatigue among the vibration waveform of fatigue and alertness (S52). This is because the fact that the driver sits down again while actuators 140 are not driven may start to get tired. In such a case, by vibrating actuators 140 with the vibration waveform for fatigue, controller 160 can effectively reduce driver fatigue. When actuators 140 are driven with the vibration waveform for fatigue, controller 160 proceeds to step S14 and continues the process.

In this way, vehicle seat 100 according to the present embodiment includes pressure sensor 150 capable of measuring the pressure distribution on the surface of the seat, a plurality of actuators 140 provided in the seat, and controller 160 that controls vibrations generated by actuators 140 based on the pressure distribution when a person sits down (for example, S12 to S15 shown in FIG. 6). Controller 160 is, for example, electrically connected to pressure sensor 150 and the plurality of actuators 140.

With this, vehicle seat 100 can cause actuators 140 to generate vibration according to the pressure distribution. The pressure distribution changes depending on the position, posture, physique, etc. of the person sitting on vehicle seat 100. That is, vehicle seat 100 can cause actuators 140 to generate vibration according to the position, posture, and physique of a sitting person. Therefore, vehicle seat 100 can appropriately transmit the vibration to the sitting person.

Vehicle seat 100 can appropriately transmit the vibration to the sitting person, as compared with the case where the vibration generated by actuators 140 is not controlled according to the pressure distribution, for example.

It should be noted that controller 160 only needs to be able to execute at least one of the operations shown in FIGS. 6 to 10.

Variation of the Embodiment

Figure 11:
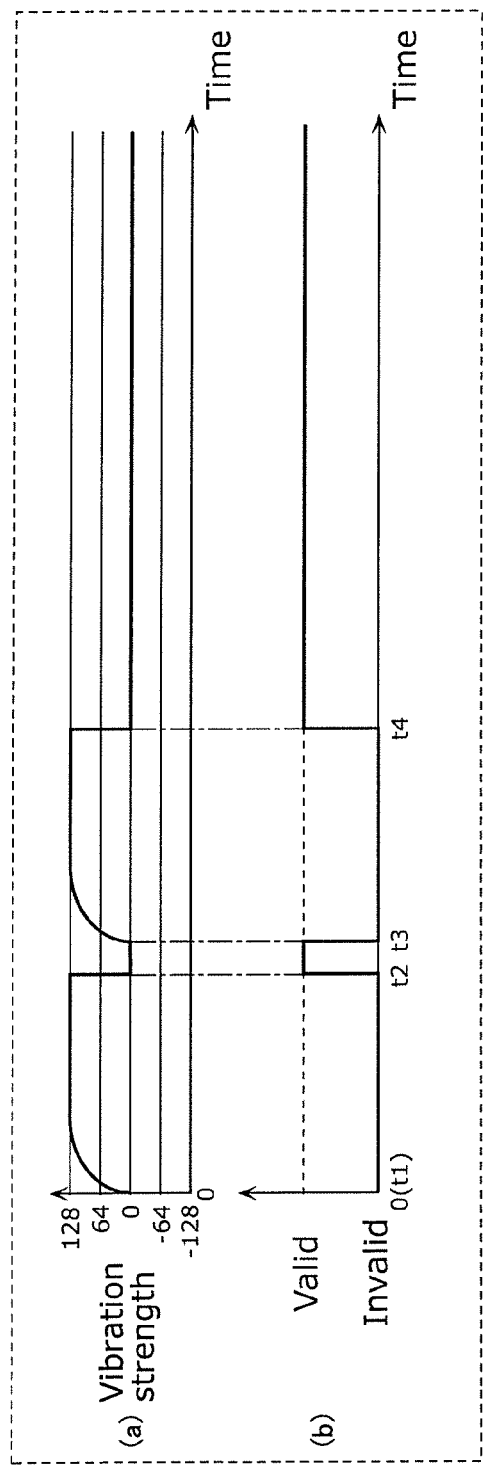
FIG. 11 is a time-dependent characteristic diagram showing a vibration waveform generated by actuators according to a variation of the embodiment and a state of the pressure sensor.

The vehicle seat according to this variation will be described below with reference to FIG. 11. FIG. 11 is a time-dependent characteristic diagram showing the vibration waveform generated by the actuator according to the present variation and the state of the pressure sensor. Specifically, (a) in FIG. 11 shows a time-dependent characteristic diagram of a vibration waveform generated by the actuator according to the present variation, and (b) in FIG. 11 shows a time-dependent characteristic diagram of a state of a pressure sensor according to the present variation. The state of the pressure sensor indicates whether the output of the pressure sensor is valid or invalid.

It should be noted that in the following description, differences from the embodiment will be mainly described, and configurations similar to those of the embodiment will be denoted by the same reference numerals, and the description may be omitted or simplified. The configuration of the vehicle seat according to this variation is the same as that of vehicle seat 100 according to the embodiment, and a description thereof will be omitted. As shown in FIG. 11, the present variation is different from the embodiment in that controller 160 invalidates the output (for example, pressure distribution) of pressure sensor 150 while actuators 140 are vibrating.

Controller 160 sets pressure sensor 150 in an invalid state for a period in which the vibration strength is not 0 as shown in (a) in FIG. 11, that is, for a period in which actuators 140 are vibrating as shown in (b) in FIG. 11. For example, when pressure sensor 150 is in an invalid state, controller 160 ignores the output from pressure sensor 150. Ignoring means that even if controller 160 acquires the output from pressure sensor 150, the vibration of actuators 140 is not controlled based on the output. In other words, controller 160 controls the vibrations of actuators 140 during the period in which pressure sensor 150 is in the invalid state, based on the output acquired from pressure sensor 150 immediately before actuators 140 generate the vibrations.

Then, controller 160 returns pressure sensor 150 to the valid state when the vibration strength becomes zero. For example, when pressure sensor 150 is in a valid state, controller 160 controls the vibrations of actuators 140 based on the output from pressure sensor 150.

In this way, controller 160 switches the state of pressure sensor 150 from one of the valid state and the invalid state to the other thereof in accordance with the operation of actuators 140. Controller 160, for example, switches the state of pressure sensor 150 from the valid state to the invalid state in synchronization with the vibration start timing (for example, times t1 and t3) of actuators 140, and switches the state of pressure sensor 150 from the invalid state to the valid state in synchronization with the vibration end timing (for example, times t2 and t4) of actuators 140.

With this controller 160 does not control the vibration based on the output of pressure sensor 150 while actuators 140 is generating the vibration. As a result, the change in the pressure distribution that actuators 140 give to pressure sensor 150 can be excluded. Therefore, since vehicle seat 100 can reduce the possibility that the posture, the physique, etc. of the sitting person will be erroneously determined due to the vibrations generated by actuators 140, the vibration can be transmitted more appropriately to the sitting person.

It should be noted that controller 160 sets pressure sensor 150 to be in an invalid state, for example, when at least one actuator 140 among the plurality of actuators 140 vibrates.

It should be noted that the configuration in which controller 160 sets pressure sensor 150 is in an invalid state is not limited to the configuration in which the output from pressure sensor 150 is ignored, and for example, controller 160 may cut off the power supply to pressure sensor 150 so that the pressure distribution signal from pressure sensor 150 is not output.

In addition, as soon as the vibration strength becomes 0, pressure sensor 150 is returned in a valid state in FIG. 11, but the configuration is not limited thereto. For example, in the case where even if controller 160 controls actuators 140 so as to set the vibration strength to 0, the vibration does not immediately stop due to the inertia of actuators 140, the waiting period until the vibration actually stops is obtained in advance, and after controller 160 controls the vibration strength to 0, pressure sensor 150 may be set to the valid state after the waiting period elapses.

It should be noted that controller 160 may measure the pressure distribution based on the difference between the maximum value and the minimum value of the pressure during the predetermined measurement period. Even with this configuration, it is possible to suppress an erroneous determination in the immediate measurement of pressure sensor 150. For example, when the difference is larger than the predetermined value, it is determined that a user is not tired, and when the difference is equal to or less than the predetermined value, it is determined that the user is tired because the posture is substantially the same.

In addition, in the above variation, controller 160 may measure the pressure distribution based on the integrated pressure value during the predetermined measurement period at each coordinate point determined by the resolution of the pressure distribution of pressure sensor 150. That is, controller 160 may generate the pressure distribution based on the integrated pressure value in each coordinate point during the predetermined measurement period. The specific configuration in this case is as follows.

In order to obtain the pressure distribution (contour lines based on the pressure height) as shown in FIGS. 4 and 5, a configuration in which a plurality of sensor elements are disposed as pressure sensor 150 on the seat surface can be considered. In this case, it is required to dispose the number of sensor elements that can obtain the resolution enough to obtain the pressure distribution. For example, a plurality of sensor elements are disposed on the seat surface with a resolution of about 1 to 2 cm. Therefore, this resolution determines the coordinates of each sensor element on the seat surface.

Controller 160 may obtain a pressure distribution as shown in FIGS. 4 and 5 based on signals from a plurality of sensor elements at respective coordinate points. Then, when the sitting person moves only slightly, in order to reliably detect the change from each of the plurality of sensor elements of each coordinate point, controller 160, controller 160 is configured to integrate the pressure signals from the plurality of sensor elements of each coordinate point during a predetermined measurement period for each coordinate point. For example, assuming that the predetermined measurement period is 100 msec, the pressure signals from the plurality of sensor elements are integrated for 100 msec, respectively. With this, the integrated pressure value over a predetermined measurement period can be obtained even with a slight movement of a person, so that it is possible to detect an enhanced signal by integrating the amount of the slight movement. It should be noted that controller 160 may obtain the integrated pressure value when there is almost no change in the pressure distribution obtained from pressure sensor 150. In addition, controller 160 may repeatedly obtain the integrated pressure value for each predetermined measurement period as long as the state in which the pressure distribution hardly changes continues. It should be noted that the predetermined measurement period is not limited to 100 msec. The predetermined measurement period is, for example, a period shorter than the first period, and is only needed to be a period in which a slight movement of a person can be detected.

With such an operation, when the driver is in substantially the same posture for the first time as described in step S12 of FIG. 6, it is determined that the driver is tired, but the determination accuracy can be improved. That is, some drivers may move their posture during driving so as not to get tired, but a slight movement cannot be detected by the immediate measurement of pressure sensor 150, so that there is a possibility that the driver is mistaken for being in the substantially same posture, that is, being tired. Therefore, when it is determined that the posture is substantially the same for the first time, controller 160 measures the pressure distribution based on the integrated pressure value during the predetermined measurement period. Then, when it is determined that the posture is substantially the same even based on this pressure distribution, controller 160 determines that the driver is tired. By this operation, it is possible to particularly improve the accuracy in the determination for the driver's fatigue.

Figure 12:
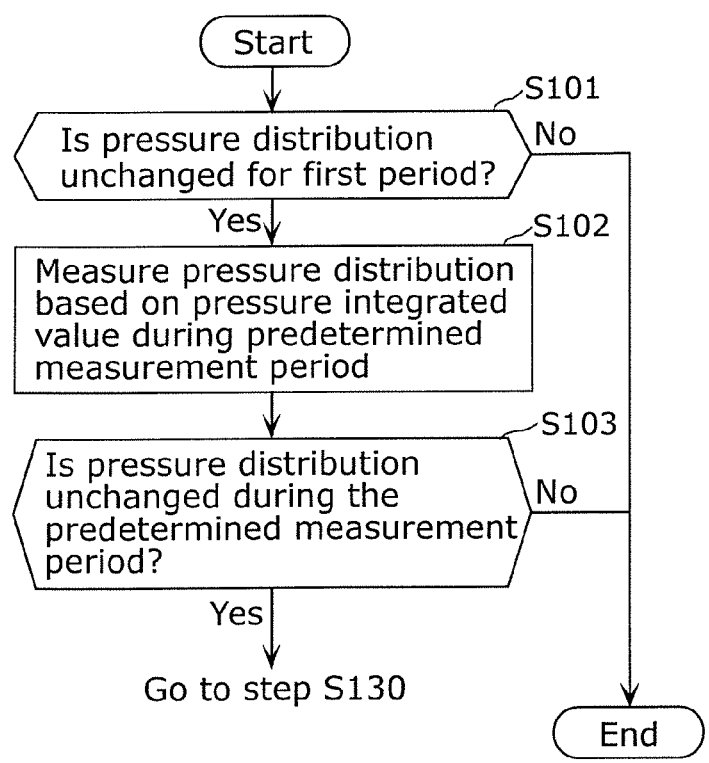
FIG. 12 is a flowchart showing an example of the operation of the vehicle seat according to the variation of the embodiment.

Here, an operation of determining (judging) whether or not the postures are substantially the same using the pressure distribution based on the integrated pressure value according to the present variation will be described with reference to FIG. 12. FIG. 12 is a flowchart showing an example of the operation of vehicle seat 100 according to the present variation. FIG. 12 shows an example of the determination process shown in step S12 of FIG. 6 as to whether or not there is no change in the pressure distribution for the first time and the operation performed between the determination process and step S13.

As shown in FIG. 12, controller 160 determines whether or not there is no change in the pressure distribution acquired from pressure sensor 150 for the first time (S101). The determination process of step S101 corresponds to the determination process shown in step S12 of FIG. 6 as to whether or not there is no change in the pressure distribution for the first time.

When there is no change in the pressure distribution for the first time (Yes in S101), that is, when the driver has substantially the same posture for the first time, controller 160 further measures the pressure distribution based on the integrated pressure value during the predetermined measurement period (S102). Controller 160 integrates pressure signals from a plurality of sensor elements of each coordinate point configuring pressure sensor 150 for each coordinate point (for each sensor element) during a predetermined measurement period. With this, the integrated pressure value obtained by integrating the pressure signals in the predetermined measurement period is calculated for each coordinate point. Controller 160 measures the pressure distribution by generating the pressure distribution based on the integrated pressure value for each coordinate point. It should be noted that the predetermined measurement period is a period after the first period.

Next, controller 160 determines whether or not there is no change in the pressure distribution during the predetermined measurement period (S103). The fact that there is a change in the pressure distribution may mean, for example, that the position of the peak value of the integrated pressure value or the distribution of the region equal to or larger than the predetermined integrated pressure value in the pressure distribution measured by pressure sensor 150 is different from the position of the peak value of the integrated pressure value or the distribution of the region equal to or larger than the predetermined integrated pressure value in the pressure distribution used for the determination in step S101. In addition, the fact that there is a change in the pressure distribution may mean, for example, that the position of the peak value of the integrated pressure value or the region equal to or larger than the predetermined integrated pressure value in the pressure distribution of each of two predetermined measurement periods that are temporally continuous with each other is different.

It should be noted that the fact that the pressure distribution does not change in the above includes that it does not change substantially.

Next, when it is determined as Yes in step S103, that is, when it is determined that the driver is in substantially the same posture even in the determination using the integrated pressure value, controller 160 determines that the driver is tired, and the process proceeds to step S13 shown in FIG. 6 to drive actuators 140 with the vibration waveform for fatigue.

In addition, when it is determined as No in step S101, that is, when the driver is moving, controller 160 determines that the driver is not tired and ends the process. Furthermore, in the present variation, when it is determined as Yes in step S101 and No in step S103, that is, when the driver is slightly changing the posture during driving so as not to get tired, controller 160 determines that the driver is not tired and ends the process. This can prevent the driver from being erroneously determined to be tired.

Other Embodiments

Vehicle seat 100 according to one or more aspects has been described above based on the embodiment, but the present disclosure is not limited to this embodiment. Without departing from the spirit of the present disclosure, the present disclosure may include embodiments in which various variations that one of skilled in the art can conceive are applied to the present embodiment, and embodiments configured by combining components in different embodiments.

For example, in the embodiment described above, such an example that the first time and the second time are constant times has been described, but the present invention is not limited thereto. At least one of the first time or the second time may vary depending on the accumulated time after the ignition is turned on. For example, at least one of the first time or the second time may be set shorter as the accumulated time after the ignition is turned on increases. The setting of the first time and the second time is executed, for example, by controller 160.

In addition, such an example that it is determined in step S12 whether or not the pressure distribution has no change for the first time or the operation exceeds the second time has been described in FIG. 6 in the embodiment described above, but the present disclosure is not limited thereto. If the determination process of whether or not the pressure distribution has no change for the first time is step S12a and the determination process of whether or not the operation exceeds the second time is step S12b, for example, when it is determined as No (when the pressure distribution changes within the first time) in step S12a, the determination in step S12b may be performed. Then, when it is determined as Yes in step S12b, the process proceeds to step S13, and when it is determined as o in step S12b, the process returns to step S12a. When the accumulated time of the first time exceeds the second time because the No determination is continuously generated in step S12a, it is determined as Yes in step S12b, and the process proceeds to step S13 and automatically actuators 140 starts operating with the vibration waveform for fatigue.

In addition, such an example that controller 160 drives actuators 140 at a constant frequency when actuators 140 are driven with the vibration waveform for fatigue or alertness has been described in the embodiments described above, but the present disclosure is not limited thereto. Controller 160 may control actuators 140, for example, such that the frequency changes with time in a frequency range suitable for fatigue or alertness.

In addition, controller 160 may obtain a warning signal from outside the vehicle in which vehicle seat 100 is mounted in the embodiments described above. Controller 160 may obtain, for example, traffic jam information, accident information, or the like in the traveling direction as a warning signal from a server device. Such information may be obtained from, for example, a navigation system mounted on the vehicle.

In addition, the order in which the steps in the flowchart are executed is an example for specifically describing the present disclosure, and may be an order other than the above. In addition, some of the steps described above may be executed simultaneously (in parallel) with other steps.

In addition, some or all of the components included in vehicle seat 100 according to the embodiments described above and the like may be configured by one system LSI (Large Scale Integration).

The system LSI is a super multifunctional LSI manufactured by integrating a plurality of processors on one chip, and specifically, is a computer system configured to include a microprocessor, a ROM (Read Only Memory), a RAM (Random Access Memory), and the like. A computer program is stored in the ROM. The system LSI achieves the function by the microprocessor operating according to the computer program. It should be noted that all or part of the various processes described above may be realized by a hardware such as an electronic circuit.

In addition, one aspect of the present disclosure may be a computer program that causes a computer to execute each characteristic step included in the method for controlling vehicle seat 100. In addition, one aspect of the present disclosure may be a computer-readable non-transitory recording medium in which such a program is recorded. For example, such a program may be recorded in a recording medium to be distributed. For example, by installing the distributed program in a device having another processor and causing the processor to execute the program, it is possible for the device to perform each of the processes described above.

While various embodiments have been described herein above, it is to be appreciated that various changes in form and detail may be made without departing from the spirit and scope of the present disclosure as presently or hereafter claimed.

FURTHER INFORMATION ABOUT TECHNICAL BACKGROUND TO THIS APPLICATION

The disclosures of the following Japanese Patent Applications including specification, drawings and claims are incorporated herein by reference in their entirety: Japanese Patent Application No. 2019-184503 filed on Oct. 7, 2019, and No. 2020-097095 filed on Jun. 3, 2020.

INDUSTRIAL APPLICABILITY

The present disclosure can be used for, for example, a vehicle seat mounted on a vehicle.

The invention claimed is:
1. A vehicle seat, comprising:
a pressure sensor capable of measuring a pressure distribution on a surface of the vehicle seat;
a plurality of actuators provided in the vehicle seat; and
a controller that controls vibrations generated by the plurality of actuators based on the pressure distribution output by the pressure sensor,
wherein the controller invalidates an output of the pressure sensor for a period during which the plurality of actuators generate the vibrations and for a waiting period after the period.
2. The vehicle seat according to claim 1,
wherein when a variance value of the pressure distribution is smaller than a first threshold value, and a pressure value in the pressure distribution is equal to or larger than a second threshold value, the controller performs control to increase a strength of vibration of each of the plurality of actuators.
3. The vehicle seat according to claim 1,
wherein when a variance value of the pressure distribution is larger than a predetermined value, the controller performs control to increase a strength of a vibration of an actuator among the plurality of actuators which is disposed in a first portion where a pressure value in the pressure distribution is larger than in a second portion.
4. The vehicle seat according to claim 1,
wherein the controller controls the vibrations of the plurality of actuators based on a warning signal from outside the vehicle seat.
5. The vehicle seat according to claim 4,
wherein the controller controls at least one of a frequency or a strength of each of the vibrations of the plurality of actuators based on a type of the warning signal.
6. The vehicle seat according to claim 1,
wherein when the pressure distribution does not substantially change over a first period, the controller controls the plurality of actuators with at least one of a frequency or a strength to reduce fatigue.
7. The vehicle seat according to claim 1,
wherein when the pressure distribution fluctuates in a constant cycle within a second period, the controller controls the actuators with at least one of a frequency or a strength for promoting alertness.
8. The vehicle seat according to claim 1,
wherein when a pressure width of the pressure distribution changes more than a third threshold within a third period, the controller controls the actuator with at least one of a frequency or a strength to reduce fatigue.
9. The vehicle seat according to claim 1,
wherein the controller measures the pressure distribution based on an integrated pressure value during a prede- termined measurement period at each coordinate point determined by a resolution of the pressure distribution of the pressure sensor.

10. The vehicle seat according to claim 9, wherein when the pressure distribution does not substantially change over a first period, the controller measures the pressure distribution based on the integrated pressure value.

11. The vehicle seat according to claim 10, wherein the controller determines whether or not the pressure distribution changes substantially over the first period.

12. The vehicle seat according to claim 10, wherein when the pressure distribution based on the integrated pressure value does not substantially change, the controller controls the plurality of actuators with at least one of a frequency or a strength to reduce fatigue.

13. The vehicle seat according to claim 6, wherein the first period is an elapsed time after the pressure distribution has not changed substantially.

14. The vehicle seat according to claim 7, wherein the second period is an elapsed time after an ignition is turned on in the vehicle on which the vehicle seat is mounted, or an elapsed time after the vehicle is stopped for a predetermined time or longer.

15. The vehicle seat according to claim 8, wherein the third period is a period in which it is possible to determine that a sitting driver has reseated.

16. The vehicle seat according to claim 1, wherein the pressure sensor and the plurality of actuators are provided in each of a seat cushion and a seat back of the vehicle seat.

17. A vehicle seat, comprising:
a pressure sensor capable of measuring a pressure distribution on a surface of the vehicle seat;
a plurality of actuators provided in the vehicle seat; and
a controller that controls vibrations generated by the plurality of actuators based on the pressure distribution output by the pressure sensor,
wherein when a variance value of the pressure distribution is smaller than a first threshold value, and a pressure value in the pressure distribution is equal to or larger than a second threshold value, the controller performs control to increase a strength of vibration of each of the plurality of actuators.

18. A vehicle seat, comprising:
a pressure sensor capable of measuring a pressure distribution on a surface of the vehicle seat;
a plurality of actuators provided in the vehicle seat; and
a controller that controls vibrations generated by the plurality of actuators based on the pressure distribution output by the pressure sensor,
wherein when a variance value of the pressure distribution is larger than a predetermined value, the controller performs control to increase a strength of a vibration of an actuator among the plurality of actuators which is disposed in a first portion where a pressure value in the pressure distribution is larger than in a second portion.

* * * * *